(12) United States Patent
Weitekamp et al.

(10) Patent No.: US 9,776,242 B2
(45) Date of Patent: Oct. 3, 2017

(54) MULTIPHOTON INDUCED DIRECT AGGREGATE SCRIBING

(71) Applicant: CALIFORNIA INSTITUTE OF TECHNOLOGY, Pasadena, CA (US)

(72) Inventors: Raymond Weitekamp, Glendale, CA (US); Krishnan Thyagarajan, Pasadena, CA (US); Jacob Berlin, Duarte, CA (US); Desiree Van Haute, Duarte, CA (US)

(73) Assignees: California Institute of Technology, Pasadena, CA (US); City of Hope, Duarte, CA (US)

( * ) Notice: Subject to any disclaimer, the term of this patent is extended or adjusted under 35 U.S.C. 154(b) by 0 days.

(21) Appl. No.: 15/071,544

(22) Filed: Mar. 16, 2016

(65) Prior Publication Data

US 2016/0271694 A1   Sep. 22, 2016

Related U.S. Application Data

(60) Provisional application No. 62/134,778, filed on Mar. 18, 2015.

(51) Int. Cl.
*B22F 1/00* (2006.01)
*G02B 5/00* (2006.01)
(Continued)

(52) U.S. Cl.
CPC ............ *B22F 1/0096* (2013.01); *G02B 5/008* (2013.01); *A61K 9/14* (2013.01); *B22F 1/0018* (2013.01);
(Continued)

(58) Field of Classification Search
CPC ...... B22F 1/003; B22F 1/0088; B22F 1/0096; B22F 1/0018; B22F 1/081; G02B 5/00; G02B 5/008; G02B 5/281; G02B 26/00; B82Y 35/00; B82Y 40/00; B29B 9/00; B29B 9/08; G02F 1/03; A61K 9/0009; A61K 9/14; A61K 9/5138; A61K 47/0043; A61K 47/0065; A61K 47/0084;
(Continued)

(56) References Cited

U.S. PATENT DOCUMENTS 7,005,229 B2 *  2/2006  Nirmal ................. G03F 7/0047
                                                        430/138
7,252,699 B2 *  8/2007  Perry .................... B22F 1/0018
                                                        148/513
(Continued)

OTHER PUBLICATIONS

Boal et al., "Self-assembly of nanoparticles into structured spherical and network aggregates", Nature, Apr. 2000, 404, 746-748.
(Continued)

*Primary Examiner* — Loha Ben
(74) *Attorney, Agent, or Firm* — Baker & Hostetler, LLP (57) ABSTRACT

The present disclosure is directed to processes comprising irradiating an aggregate of chemically bonded or otherwise associated nanoparticles with a light source capable of providing multiphoton excitation, the light source directed at a focal point volume including the aggregate and having sufficient energy to disrupt or fuse the aggregate within the focal point volume to form nanoscale deposits of the nanoparticles.

23 Claims, 3 Drawing Sheets

(51) Int. Cl.
*G02F 1/01* (2006.01)
*G02F 1/03* (2006.01)
*B82Y 40/00* (2011.01)
*B29B 9/08* (2006.01)
*A61K 9/14* (2006.01)

(52) U.S. Cl.
CPC ................ *B29B 9/08* (2013.01); *B82Y 40/00* (2013.01); *G02F 1/01* (2013.01)

(58) Field of Classification Search
CPC ........ A61K 47/48561; A61K 47/48861; A61K 49/0001; A61K 49/0002; A61K 49/0021; A61K 49/0423; A61K 49/0093
USPC ..... 359/241, 296, 350, 452; 424/489; 264/5, 264/6; 252/582, 587
See application file for complete search history.

(56) References Cited

U.S. PATENT DOCUMENTS

| | | | | |
|---|---|---|---|---|
| 7,381,516 | B2 * | 6/2008 | Arney | B82Y 10/00 430/170 |
| 7,985,367 | B2 * | 7/2011 | Hiromatsu | B82Y 30/00 264/21 |
| 8,345,364 | B2 * | 1/2013 | Liberman | G02B 5/008 359/888 |
| 8,685,293 | B1 * | 4/2014 | Coppa | B23K 26/03 264/400 |
| 9,187,318 | B2 * | 11/2015 | Duan | B23K 26/0613 |
| 9,302,116 | B2 * | 4/2016 | Vo-Dinh | A61K 49/0039 |
| 2014/0377175 | A1 | 12/2014 | Berlin et al. | |

OTHER PUBLICATIONS

Klajn et al., "Plastic and Moldable Metals by Self-Assembly of Sticky Nanoparticle Aggregates", Science, Apr. 2007, vol. 316, 261-264.

Tam et al., "Controlled Assembly of Biodegradable Plasmonic Nanoclusters for Near-Infrared Imaging and Therapeutic Applications", ACS Nano, Apr. 2010, 4(4), 2178-2184.

Zaki et al., "Gold-Loaded Polymeric Micelles for Computed Tomography-Guided Radiation Therapy Treatment and Radiosensitization", ACS Nano, 2014, 8(1), 104-112.

* cited by examiner

MULTIPHOTON INDUCED DIRECT AGGREGATE SCRIBING

CROSS REFERENCE TO RELATED APPLICATIONS

This application claims priority to U.S. Patent Application Ser. No. 62/134,778, filed Mar. 18, 2015, the contents of which are incorporated by reference in their entireties for all purposes.

TECHNICAL FIELD

This disclosure is directed to the use of multiphoton light sources in the preparation of plasmonic devices.

BACKGROUND

Plasmonics concerns itself with metal optics at the nanoscale. The ability of nanostructures to confine light in sub-wavelength dimensions and also exhibit large field enhancements makes it an important platform to understand and take advantage of light-matter interaction at these mesoscopic dimensions. The dipole antenna is one of the simplest plasmonic structures exhibiting large field enhancements in the gap.

The present disclosure provides methods capable of preparing such devices.

SUMMARY

The present invention is directed to the use of multiphoton laser sources to form nanoscale deposits from nanoparticle aggregates. The application of multiphoton excitation to suspended or otherwise positioned nanoclusters—at wavelengths largely transparent to infrared laser light—enables direct-writing of 3D nanostructures. Through multiphoton absorption by the cluster, the heating of the nanoparticles causes local sintering in a volume defined by the focal point of the optics.

Certain embodiments of the present disclosure provides processes, each process comprising irradiating an aggregate of chemically bonded or otherwise associated nanoparticles with a light source capable of providing multiphoton excitation, the light source directed to a focal point volume including (i.e., within or encompassing) the aggregate and having sufficient energy to disrupt or fuse the nanoparticles in the aggregate within the focal point volume to form nanoscale deposits of the nanoparticles. While the nature of the nanoparticles is not limited by the disclosed methods, in many aspects the nanoparticles comprise metals or metalloids, for example, including, but not limited to titanium, zirconium, gold, silver, palladium, platinum, cerium, arsenic, iron, aluminum, carbon, boron, cadmium, selenium, zinc or silicon, or an alloy or mixture thereof. The use of gold, silver, palladium, and platinum appear particularly attractive in these processes.

While the aggregates are described in some embodiments as chemically bonded, in other embodiments, the nanoparticles may be confined in space by such vesicles as micelles, emulsions, microemulsions, or liposomes. Where chemically bonded, the aggregate of chemically bonded nanoparticles may comprise covalently linked nanoparticles. Various embodiments of these containment and chemical bondings are described herein.

The nanoparticles may be defined in terms of their diameters being in a range of from about 2 nm to about 20 nm. The nanoparticle aggregates may be described as effective diameters in a range of from about 15 to about 1000 nm and having interparticle spacings in a range of from about 1 nm to about 10 nm. Other dimensions for both the nanoparticles and their aggregates may be otherwise characterized as described herein.

In independent embodiments, the nanoparticle aggregates are dispersed in solutions (aqueous or non-aqueous) or dispersed or deposited on a substrate at the time of irradiation Various light source can be used for the multiphoton excitation and its selection is generally within the purview of a person skilled in the art. For example, in certain embodiments, the light source is a pulsed infrared light, emitting wavelengths in a range of 550 nm to 1500 nm, using femptosecond scale pulses at operating powers in a range of from about 10 to 100 mW. When scanning across the nanoparticle aggregates, for example, in a direct writing mode or when preparing larger area formations, typical scan speeds can range from microns per second or millimeters per second.

Since the multiphoton excitation occurs in the focal point volume of the optics employed, causing very localized sintering in this volume, the resulting structures are nanoscaled in dimensions, and in certain embodiments, the resulting nanoscale deposits of the nanoparticles can be in a range of from 2 nm to 100 nm. In some further embodiments, the resulting nanoscale deposits are capable of exhibiting optical filtering due to surface plasmon resonances.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods of making and methods of using, processes, devices, and systems disclosed. In addition, the drawings are not necessarily drawn to scale. In the drawings:

FIG. 2(A-C) show optical images of the fabricated structures: (A) a checkerboard pattern; (B) an array of rods; and (C) an array of discs, all on quartz substrates. The brackets in (B) highlight the lengths and regularity of the formed rods.

DETAILED DESCRIPTION OF ILLUSTRATIVE EMBODIMENTS

The present invention involves use of multiphoton excitation as a tool for depositing nanoscale structures, preferably metallic structures, from dispersed or deposited nanoparticle aggregates. The use of multiphoton excitation allows for the selective nanoscale writing obtained from such aggregate systems.

The present invention may be understood more readily by reference to the following description taken in connection with the accompanying Figures and Examples, all of which form a part of this disclosure. It is to be understood that this invention is not limited to the specific products, methods, processes, conditions or parameters described or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this specification, claims, and drawings, it is recognized that the descriptions refer to compositions and processes of making and using said compositions. That is, where the disclosure describes or claims a feature or embodiment associated with a method or process of making or using a composition, it is appreciated that such a description or claim is intended to extend these features or embodiment to embodiments directed to the corresponding compositions, and vice versa (i.e., in contexts including the compositions, methods of making, and methods of using).

Certain embodiments provide for processes, each process comprising irradiating an aggregate of chemically bonded or otherwise contained nanoparticles with a light source capable of providing multiphoton excitation, the light source directed at a focal point volume focal point volume including (i.e., within or encompassing) the aggregate and having sufficient energy to disrupt or fuse the nanoparticles in the aggregate within the focal point volume focal point volume to form nanoscale deposits of the nanoparticles.

Multiphoton excitation or absorption is a non-linear optical process defined by the near simultaneous absorption of two or more photons, of identical or different frequencies, that excites a molecule or other species (preferably metallic) from one state (usually the ground state) to a higher energy electronic state. This higher excited state is otherwise energetically inaccessible by the absorption of a single photon of the same energy. Because the process requires high laser power and tight beam focusing, multiphoton excitation occurs only in a small volume (i.e., "voxel volume) in the immediate vicinity of the focal point of the irradiating laser and other materials outside this volume are exposed only to isolated low-energy photons.

The dimensions of the deposited particles may be even smaller than these voxel volumes. Without intending to be bound by the correctness of any particular theory, in the present processes, it appears that the mechanism being exploited is the extreme field localization and generation of heat within the nanogaps between the particles constituting the nanoclusters. In this case, the fusion of the nanoparticles takes place where the fields are enhanced. When light of an appropriate wavelength is shone on a metallic nanostructure, plasmon resonances can cause field localization within a focal volume which is much smaller than the 'focal volume' of the impinging light. In these circumstances, the field is enhanced by many orders of magnitude, and 'hot spots' are formed. Thus it is possible to have a voxel volume larger than the dimensions of the deposits, since the factor dictating the dimensions are the field localizations which are in turn determined by the nanogaps.

In certain embodiments, the nanoparticles comprise metals or metalloids. In other independent embodiments, the nanoparticles may comprise electrically conducting materials (for example, pure metals or alloys or doped carbon) or semiconducting (including optionally doped Si, GaAs, InP, ZnS, CdS, PbS).

Clearly more preferred are those embodiments where the nanoparticles comprise titanium, zirconium, gold, silver, palladium, platinum, cerium, arsenic, iron, aluminum, carbon, boron, cadmium, selenium, zinc or silicon, or an alloy or mixture thereof. It should be appreciated that any subset of these materials represents another embodiment, for example including those where the nanoparticles comprise titanium, zirconium, gold, silver, platinum, palladium, cerium, arsenic, iron, aluminum, or zinc, or an alloy or mixture thereof. Additional embodiments include those where the nanoparticles comprise noble metal plasmonic elements, such as gold, silver, platinum, or palladium, or any alloy or mixture thereof. Gold appears to be particularly useful in these processes.

Chemical bonding between nanoparticles is one means of forming and maintaining the structure of such aggregates, and in certain embodiment, the aggregate of nanoparticles comprises such covalent bonds. However, the nanoparticles need not be covalently bonded, but may rather be held proximate (e.g., according to the nanoparticle spacings described elsewhere herein) by confinement by external structures, such as micelles, emulsions, microemulsions, or liposomes.

In some embodiments, the nanoparticles in the aggregate have a mean particle diameter in a range of from about 2 nm to 4 nm, from 4 nm to 6 nm, from 6 nm to 8 nm, from 8 nm to 10 nm, from 10 nm to 12 nm, from 12 nm to 14 nm, from 14 nm to 16 nm, from 16 nm to 18 nm, from 18 nm to 20 nm, from 20 nm to 40 nm, from 40 nm to 60 nm, from 60 nm to 80 nm, from 80 nm to 100 nm, from 100 nm to 200 nm, from 200 nm to 400 nm, or a range combining any two or more of these ranges, for example, from 2 nm to 10 nm. The particles may be independently described as monomodal, bimodal, polymodal, or polydispersed in their distributions and packing architectures.

Lengths and sizes of nanoparticles and nanoparticle aggregates as described herein may be measured using Transmission Electron Microscopy using statistical analyses of visual observation, or other suitable method. In one embodiment, the transmission electron microscopy measurements may be obtained by drying 2 microliters (or other volume) of solution onto a 200 mesh carbon copper grid (for example, from TED Pella). TEM images can then be taken using FEI Tecnai 12 Twin. In some cases, images were analyzed using a Matlab program that found the edges of each aggregate/particle by identifying transitions in contrast in the TEM images and then calculating the area of each aggregate/particle in the image, the area being converted to diameter by assuming a circular shape of the aggregate/particle. The diameters described in this disclosure represent the means of the measured diameters. Lengths and sizes (e.g., hydrodynamic diameters) may also be measured by dynamic light scattering (DLS) as described herein.

In some embodiments, the nanoparticles within these aggregates are spaced by a distance in a range of from about 1 nm to 1.5 nm, from 1.5 nm to 2 nm, from 2 nm to 2.5 nm, from 2.5 nm to 3 nm, from 3 nm to 3.5 nm, from 3.5 nm to 4 nm, from 4 nm to 4.5 nm, from 4.5 nm to 5 nm, from 5 nm to 6 nm, from 6 nm to 8 nm, from 8 nm to 10 nm, from 10 nm to 12 nm, from 12 nm to 14 nm, from 14 nm to 16 nm, from 16 nm to 18 nm, from 18 nm to 20 nm, or a range combining any two or more of these ranges, for example, from 1.5 nm to 2.5 nm or from 1 nm to 5 nm.

The aggregates can comprise tens, hundreds, or even thousands of associated nanoparticles, so as to provide aggregate superstructures which can be described in terms of a mean diameter in a range of from about 10 nm to 15 nm, from 15 nm to 20 nm, from 20 nm to 25 nm, from 25 nm to 30 nm, from 30 nm to 50 nm, from 50 nm to 80 nm, from 80 nm to 110 nm, from 110 nm to 140 nm, from 140 nm to 170 nm, from 170 nm to 200 nm, from 200 nm to 250 nm, from 250 nm to 300 nm, from 350 nm to 400 nm, from 400 nm to 45 nm, from 450 nm to 500 nm, from 500 nm to 600 nm, from 600 nm to 700 nm, from 700 nm to 800 nm, from 800 nm to 900 nm, from 900 nm to 1000 nm, from 1000 nm to 1200 nm, from 1200 nm to 1400 nm, from 1400 nm to 1600 nm, from 1600 nm to 1800 nm, from 1800 nm to 2000 nm, or a range combining any two or more of these ranges, for example, from 50 nm to 200 nm or from 80 nm to 120 nm.

In some embodiments of the instant disclosure, the nanoparticle aggregates comprise chemically bonded nanoparticles, for example comprising covalently linked nanoparticles. These linked nanoparticles comprise so-called "chemical spacers" comprising optionally substituted 2 to 50 membered alkylene or heteroalkylene linkages, optionally substituted 3 to 20 membered cycloalkylene or heterocycloalkylenes or optionally substituted 5 to 20 membered arylene or heteroarylenes, or combinations thereof. The spacer linkages may be linear or branched; if branched, the length of the spacer applies to each pair of the branching unit. Additionally, within the aggregate, each nanoparticle may be further stabilized by non-linking ligands, for example mono-, di-, or polyvalent moieties. Such moieties can be organic alcohols, amines, carboxylic acids or thiols, or combinations thereof.

As used herein, the term "chemical spacer" refers to a linkage whose purpose is to separate the nanoparticles by a specific distance, without necessary regard as to the specific nature of the linkage. Having said this, for the sake of completeness, in certain embodiments, these spacer linkages may comprise one or more of —C(O)—, —C(O)O—, —O—, —S—, —NH—, —NR$^1$—, —C(O)NR$^2$—, —S(O)$_n$—, —S(O)NR$^3$—, —OP(O)(OR$^4$)O—, —N=N—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, an amino acid sequence linker, or a nucleic acid sequence moiety, where R$^1$, R$^2$, R$^3$, R$^4$, are independently at each occurrence hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n is 1 or 2.

Additionally, these covalent chemical spacers may be defined in terms of the way in which these ligands bind to the nanoparticle. The skilled artisan would appreciate that the moiety actually binding to the nanoparticle depends on the nature of nanoparticle itself, but generally includes at least one functional group comprising a C, N, O, P, or S atom, for example (but not limited to) isocyanate, π-bonded arenes or heteroarenes, primary or secondary amines, nitriles, carboxy acids, phosphine, or thiol moieties. Thiol moieties are particularly attractive for gold nanoparticles and amino groups are attractive options for other noble metal plasmonic elements.

In other embodiments, the nanoparticle aggregates comprise nanoparticles containing ligands which bind to a common polymer, so as to replicate the effect of a spacer linkage.

In still other embodiments, the nanoparticle aggregates comprise nanoparticles are contained with polymeric structures, such as a micelle, emulsion, microemulsion, or liposome. The boundaries of these polymeric "corrals" may comprise oligomeric or polymeric compounds, often used as surfactants, for example including polyalkylene glycols (e.g., polymers or copolymers of ethylene glycol, EG, or propylene glycol, PG), polylactic acid, polyglyolic acids, poly(lactide-co-glycolide) (PLGA), poly(amino acids), copoly(ether-esters), oxidized cellulose, polycarbonate, poly (vinyl alcohol), peptides, polypeptides, proteins, polysaccharides, polynucleotides, polycaprolactone (PCL), polydioxanone (PDO), trimethylene carbonate (TMC), alginate or alginic acid, chitosan polymers, or copolymers or mixtures thereof.

The nanoparticle aggregates of the present disclosure may be dispersed in a solvent or may be present near or deposited on a substrate when irradiated. The solvent may be aqueous or non-aqueous, protic or aprotic. Suitable solvents include, but are not limited to water, lower alcohols (e.g., methanol or ethanol), chloroform, dichloromethane, dimethylformamide, dimethylacetamide, tetrahydrofuran, 2-methyltetrahydrofuran, and the like. When dispersed in aqueous solutions, the solvent may include one or more of an electrolyte salt, surfactant, or other additive.

When the nanoparticles aggregates are present near or deposited on a substrate, the substrate is preferably, but not necessarily capable of reflecting the incident light. Exemplary surfaces comprise semiconductor materials (for example silicon, GaAs, InP, including their oxide coatings), metals (e.g., aluminum, steel, stainless steel), glasses (including fused silica, borosilicate, aluminosilicate, and silicate glasses, and quartz), and polymers (e.g., poly(methyl methacrylate).

Within these contexts, there are a number of systems which are applicable for use with the disclosed processes. Each of these references describes strategies consistent with the parameters cited herein, and the various embodiments described or readily apparent to the skilled artisan from these teachings, or combinations of these teachings, are considered independent embodiments of the instant disclosure. For the sake of completeness, these references are incorporated by reference herein in their entirety, and especially for their teaching of the compositions described for the nanoparticles, the methods of assembling the nanoparticle aggregates, and the nanoparticle aggregates themselves.

For example, U.S. patent application Ser. No. 14/313,736 ("the '736 application"), filed Jun. 24, 2014 describes class of nanoparticle aggregates described in terms of a plurality of interior nanoparticle cores bound together and enclosed by a plurality of exterior nanoparticle cores bound together by linking groups, wherein at least a portion of the plurality of interior nanoparticle cores are bound to the plurality of exterior nanoparticle cores. The nanoparticulate structures and components used to prepare these structures are consistent with, and have been used in the processes described in the instant disclosure.

In other embodiments, the processes are applicable for use with the systems described by Tam et al. *ACSNano*, 4(4), 2178-2184 (2010), this reference also being incorporated by reference herein in its entirety for all purposes. This Tam reference teaches, inter alia, biodegradable nanoclusters comprising sub-5 nm gold particles stabilized with citrate ligands and a small amount of a weakly adsorbed biodegradable triblock copolymer of polylactic acid and polyethylene glycol, PLA(2K)-b-PEG(10K)-b-PLA(2K). This strategy of using a tri-block copolymer provides an effective means of providing the aggregates useful in the present disclosure. Tam's resulting nanoclusters were shown to exist as aggregates having a measured diameter of 83.0±4.6 nm.

Interparticle distances between constituent gold particles within the cluster were estimated to be 1.80±0.6 nm based on TEM imaging. This spacing was said to be consistent with the length scale of a lysine-lysine dipeptide in solution of 1.49 nm.

In still other embodiments, the processes are applicable for use with the systems described by Rafal Klajn et al., *Science*, Vol 316(13) April 2007. In this reference, aggregated nanoparticle assemblies (described as "supraspheres") comprising ca. 5 nm spheres of Au, Ag, Pt, Pd, and mixtures thereof were prepared in toluene and assembled with dithiol azobenzene cross-linker [4,4'-bis(11-mercaptoundecanoxy) azobenzene (ADT)] linking groups. The nanoparticles were further stabilized by dodecylamine (DDA) capping agent and didodecyldimethylammonium bromide (DDAB) surfactant. The dimension of the linking group was consistent with an appropriate interparticle spacing for use in the instant processes. The supraspheres were shown to have effective diameters between about 50 and 300 nm, consistent with the processes described herein.

In still another embodiment, the processes are applicable for use with the systems described by Ajlan Al Zaki, et al *ACSNano*, 8(1), 104-112 2014. In this reference, gold nanoparticles (1.9 nm diameter), capped with dodecanethiol, were encapsulated within the hydrophobic core of micelles formed with the amphiphilic diblock copolymer poly(ethylene glycol)-b-poly(ε-caprolactone). These gold loaded micelles had mean hydrodynamic diameters ranging from 25 to 150 nm and were reported to be soluble in aqueous solutions owing to the hydrophilic PEG corona of the diblock copolymer.

In still another embodiment, the processes are applicable for use with the systems described by Andrew K. Boal, et al, *Nature* 404 (13), 746-748. April 2000). In this reference, 2-nm gold particles, derivatized with thymine-functionalized alkanethiol, were assembled into spherical aggregates of size 97±17 nm, by the reaction of the thymine with diaminotriazine functionalized polystyrene. The corresponding interparticle distances were determined to be 4.4 nm, providing the aggregate dimensions and spacings attractive for use in these processes.

To this point, the processes have been defined in terms of irradiating an aggregate of nanoparticles with a light source capable of providing multiphoton excitation, the light source directed to a focal point volume including (i.e., within or encompassing) the aggregate. In certain embodiments, this light source is a pulsed infrared light. In principle the light source may provide any wavelength whose half corresponds to a significant absorption feature in the aggregate. For example, where the aggregate absorbs light at a wavelength including 390 nm, a useful laser will emit at a wavelength including 780 nm, which corresponds to a second harmonic of 390 nm. In certain embodiments, then, the light sources provides at least one wavelength of sufficient energy within a range of about 560 nm to 600 nm, from 600 nm to 640 nm, from 640 nm to 680 nm, from 680 nm to 720 nm, from 720 nm to 760 nm, from 760 nm to 800 nm, from 800 nm to 840 nm, from 840 nm to 880 nm, from 880 nm to 920 nm, from 920 nm to 960 nm, from 960 nm to 1000 nm, from 1000 nm to 1040 nm, from 1040 nm to 1080 nm, from 1080 nm to 1120 nm, from 1120 nm to 1160 nm, from 1160 nm to 1200 nm, from 1200 nm to 1240 nm, from 1240 nm to 1280 nm, from 1280 nm to 1320 nm, from 1320 nm to 1360 nm, from 1360 nm to 1400 nm, from 1400 nm to 1440 nm, from 1440 nm to 1480 nm, from 1480 nm to 1520 nm, from 1520 nm to 1560 nm, from 1560 nm to 1600 nm, or a range combining any two or more of these ranges, for example, from 600 nm to 880 nm or from 640 nm to 820 nm.

When pulsed infrared light is used, the typical pulse duration is in a range of from 20 femtosecond (fs) to 40 fs, from 40 fs to 60 fs, from 60 fs to 80 fs, from 80 fs to 100 fs, from 100 fs to 120 fs, from 120 fs to 140 fs, from 140 fs to 160 fs, from 160 fs to 180 fs, from 180 fs to 200 fs, or a range combining any two or more of these ranges, for example, from 80 fs to 120 fs.

Within this context, the light source is delivering light at an operating power in a range of 10 to 20 mW, from 20 to 40 mW, from 40 to 60 mW, from 60 to 80 mW, from 80 to 100 mW, from 100 to 120 mW, from 120 to 140 mW, from 140 to 160 mW, from 160 to 180 mW, from 180 to 200 mW, or a range combining any two or more of these ranges, for example, from 80 mW to 100 mW. The specific intensity of light depends on the aggregate type under consideration.

Each combination of wavelength, pulse duration, and operating power is considered an independent embodiment, as if stated separately.

Where the pulsed laser is operating as an instrument of direct writing, the speed of the scan depends again on the nature of the aggregate being used can be in a range of from 20 to 200 micron/second. Typical scanning speeds used in the Example were on the order of 100 micron/s. But again, the scan speeds can be adjusted accordingly to the particular system. For larger patterns, speeds as high as 40 mm/s proved useful, thereby allowed for the patterning of larger areas in shorter times.

Figure 1:
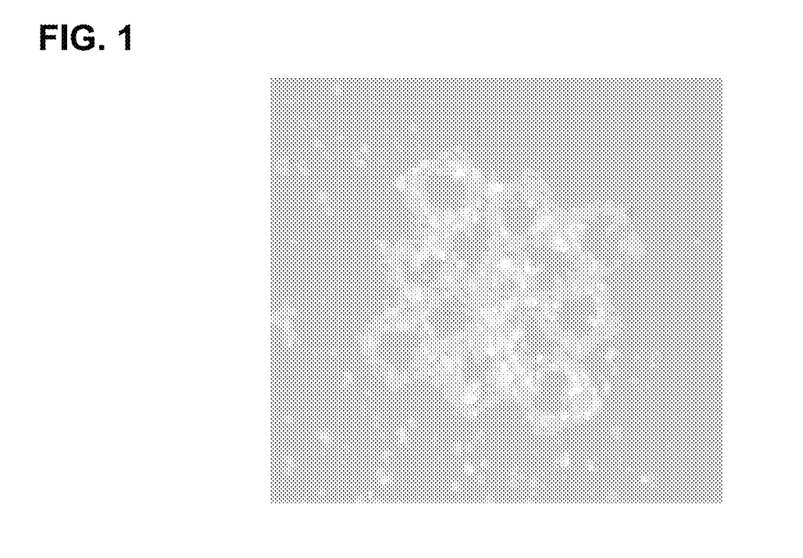
FIG. 1 shows microscope images of a rectangular array patterned using methods of the present disclosure. Each square in the 3×3 array has an approximate side length of 25 microns.

When applied, the processes provide for nanoscale deposits of the fused nanoparticles, wherein at least one dimension of the deposits of the nanoparticles is in the nanoscale range. Such structures can have at least one dimension in a range of from 2 nm to 10 nm, from 10 nm to 25 nm, from 25 to 50 nm, from 50 to 100 nm, from 100 to 200 nm, from 200 to 300 nm, from 300 to 400 nm, from 400 to 500 nm, from 600 to 700 nm, from 700 to 800 nm, from 800 to 900 nm, from 900 to 1000 nm, or a range combining any two or more of these ranges, for example, from 2 nm to 25 nm. These deposits may include curvilinear, circular, or polygonal shaped objects, when presented on a surface, or obloid or other 3-dimensional shaped objects when generated from bulk solutions. Several exemplary patterns and structures are shown in FIG. 1.

The resulting nanoscale deposits may also exhibit optical filtering due to surface plasmon resonances. A surface plasmon polariton is the coherent excitation of an electron and a photon, typically found at the interface between a metal and a dielectric. Metallic structures with nanoscale geometries represent an important class of optical materials, enabling nanophotonic confinement, waveguiding and filtering. For example, 2D periodic arrays of metallic cylinders or cylindrical hole arrays in a metal represent a simple geometries for tuning the plasmon resonance of a nanophotonic filter. FIG. 2(C) exhibits such an array. In 3D, metallic corkscrews have been used to selectively filter circularly polarized light. These plasmonic materials may also be referred to as metamaterials. Accordingly, optical filters prepared by any of the disclosed methods are also within the scope of this disclosure.

Terms

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. Similarly, unless otherwise specified, a given value carries with it the term "about" as an independent embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment as if separately stated. Conversely, various features of the invention that are, for brevity, described in the context of a single embodiment, may also be provided separately or in any sub-combination. Finally, while an embodiment may be described as part of a series of steps or part of a more general structure, each said step may also be considered an independent embodiment in itself, combinable with others.

The transitional terms "comprising," "consisting essentially of," and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method or process steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents), also provide, as embodiments, those which are independently described in terms of "consisting of" and "consisting essentially of" as if separately stated.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C." As such, any listed presented may be seen as providing embodiments that exclude any one or more members of the list.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are described herein.

The terms "aggregates," "nanoparticle aggregates," "nanoclusters," "nanoparticle assemblies," or the like are used interchangeably and are intended to describe the same structures.

The term "alkyl" as used herein refers to a linear, branched, or cyclic saturated hydrocarbon group typically although not necessarily containing 1 to about 24 carbon atoms, preferably 1 to about 12 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of 1 to 6 carbon atoms, and the specific term "cycloalkyl" intends a cyclic alkyl group, typically having 3 to 8, preferably 5 to 7, carbon atoms. The term "substituted alkyl" refers to alkyl groups substituted with one or more substituent groups, and the terms "heteroatom-containing alkyl" and "heteroalkyl" refer to alkyl groups in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl groups, respectively.

The term "alkylene" as used herein refers to a divalent difunctional linear, branched, or cyclic group derived from an alkyl group, where "alkyl" is as defined above.

The term "alkenyl" as used herein refers to a linear, branched, or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to about 12 carbon atoms. The term "lower alkenyl" intends an alkenyl group of 2 to 6 carbon atoms, and the specific term "cycloalkenyl" intends a cyclic alkenyl group, preferably having 5 to 8 carbon atoms. The term "substituted alkenyl" refers to alkenyl groups substituted with one or more substituent groups, and the terms "heteroatom-containing alkenyl" and "heteroalkenyl" refer to alkenyl groups in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl groups, respectively.

The term "alkenylene" as used herein refers to a divalent difunctional linear, branched, or cyclic group derived from an alkenyl group, where "alkenyl" is as defined above.

The term "alkynyl" as used herein refers to a linear or branched hydrocarbon group of 2 to about 24 carbon atoms containing at least one triple bond, such as ethynyl, n-propynyl, and the like. Preferred alkynyl groups herein contain 2 to about 12 carbon atoms. The term "lower alkynyl" intends an alkynyl group of 2 to 6 carbon atoms. The term "substituted alkynyl" refers to an alkynyl group substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include a linear, branched, unsubstituted, substituted, and/or heteroatom-containing alkynyl and lower alkynyl group, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aromatic" refers to the ring moieties which satisfy the Hückel 4n+2 rule for aromaticity, and includes both aryl (i.e., carbocyclic) and heteroaryl (also called heteroaromatic) structures, including aryl, aralkyl, alkaryl, heteroaryl, heteroaralkyl, or alk-heteroaryl moieties, or oligomeric or polymeric analogs thereof.

The term "aryl" as used herein, and unless otherwise specified, refers to an aromatic substituent or structure containing a single aromatic ring or multiple aromatic rings that are fused together, directly linked, or indirectly linked (such that the different aromatic rings are bound to a common group such as a methylene or ethylene moiety). Unless otherwise modified, the term "aryl" refers to carbocyclic structures. Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom, as will be described in further detail infra.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 24 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred alkaryl and aralkyl groups contain 6 to 24 carbon atoms, and particularly preferred alkaryl and aralkyl groups contain 6 to 16 carbon atoms. Alkaryl groups include, for example, p-methylphenyl, 2,4-dimethylphenyl, p-cyclohexylphenyl, 2, 7-dimethylnaphthyl, 7-cyclooctylnaphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, or —(CO)-aralkyl, and the term "acyloxy" refers to substituents having the formula —O(CO)-alkyl, —O(CO)-aryl, or —O(CO)-aralkyl, wherein "alkyl," "aryl, and "aralkyl" are as defined above.

The terms "cyclic" and "ring" refer to alicyclic or aromatic groups that may or may not be substituted and/or heteroatom-containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic, or polycyclic. The term "acyclic" refers to a structure in which the double bond is not contained within a ring structure.

The terms "halo," "halide," and "halogen" are used in the conventional sense to refer to a chloro, bromo, fluoro, or iodo substituent.

"Hydrocarbyl" refers to univalent hydrocarbyl radicals containing 1 to about 30 carbon atoms, preferably 1 to about 24 carbon atoms, most preferably 1 to about 12 carbon atoms, including linear, branched, cyclic, saturated, and unsaturated species, such as alkyl groups, alkenyl groups, aryl groups, and the like. The term "lower hydrocarbyl" intends a hydrocarbyl group of 1 to 6 carbon atoms, preferably 1 to 4 carbon atoms, and the term "hydrocarbylene" intends a divalent hydrocarbyl moiety containing 1 to about 30 carbon atoms, preferably 1 to about 24 carbon atoms, most preferably 1 to about 12 carbon atoms, including linear, branched, cyclic, saturated and unsaturated species. The term "lower hydrocarbylene" intends a hydrocarbylene group of 1 to 6 carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and hydrocarbylene moieties, respectively.

The term "heteroatom-containing" as in a "heteroatom-containing alkylene group" or "heteroalkylene" refers to a hydrocarbon molecule or a hydrocarbyl molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include alkoxyaryl, alkylsulfanyl-substituted alkyl, N-alkylated amino alkyl, and the like. Non-limiting examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

By "substituted" as in "substituted alkyl," "substituted alkylene," "substituted aryl," and the like, as alluded to in some of the aforementioned definitions, is meant that in the alkyl, alkylene, aryl, heteroaryl, or other moiety, at least one hydrogen atom bound to a carbon (or other) atom is replaced with one or more non-hydrogen substituents. Examples of such substituents include, without limitation: functional groups referred to herein as "Fn," such as halo (e.g., F, Cl, Br, I), hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_1$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl ((CO)—O-alkyl), $C_6$-$C_{24}$ aryloxycarbonyl (—(CO)—O-aryl), halocarbonyl (—(CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO—), carbamoyl (—(CO)—NH$_2$), mono-($C_1$-$C_{24}$ alkyl)-substituted carbamoyl (—(CO)NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ haloalkyl)-substituted carbamoyl (—(CO)—NH($C_1$-$C_{24}$ alkyl)), di-($C_1$-$C_{24}$ haloalkyl)-substituted carbamoyl (—(CO)—N($C_1$-$C_{24}$ alkyl)$_2$), mono-($C_5$-$C_{24}$ aryl)-substituted carbamoyl (—(CO)—NH-aryl), di-($C_5$-$C_{24}$ aryl)substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl, thiocarbamoyl (—(CS)—NH$_2$), mono-($C_1$-$C_{24}$ alkyl)-substituted thiocarbamoyl (—(CO)—NH($C_1$-$C_{24}$ alkyl)), di-($C_1$-$C_{24}$ alkyl)-substituted thiocarbamoyl (—(CO)—N($C_1$-$C_{24}$ alkyl)$_2$), mono-($C_5$-$C_{24}$ aryl)substituted thiocarbamoyl (—(CO)—NH-aryl), di-($C_5$-$C_{24}$ aryl)-substituted thiocarbamoyl (—(CO)—N($C_5$-$C_{24}$ aryl)$_2$), di-N—($C_1$-$C_{24}$ alkyl), N—($C_5$-$C_{24}$ aryl)-substituted thiocarbamoyl, carbamido (—NH—(CO)—NH$_2$), cyano(—C≡N), cyanato (—O—C≡N), thiocyanato (—S—C≡N), formyl (—(CO)—H), thioformyl (—(CS)—H), amino (—NH$_2$), mono-($C_1$-$C_{24}$ alkyl)-substituted amino, di-($C_1$-$C_{24}$ alkyl)-substituted amino, mono-($C_5$-$C_{24}$ aryl)substituted amino, di-($C_5$-$C_{24}$ aryl)-substituted amino, $C_1$-$C_{24}$ alkylamido (—NH—(CO)-alkyl), $C_6$-$C_{24}$ arylamido (—NH—(CO)-aryl), imino (—CR=NH where R=hydrogen, $C_1$-$C_{24}$ alkyl, C5-C24 aryl, $C_6$-$C_{24}$ alkaryl, $C_6$-$C_{24}$ aralkyl, etc.), $C_2$-$C_{20}$ alkylimino (—CR—N(alkyl), where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N(aryl), where R=hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO$_2$OH), sulfonate(SO$_2$O—), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO$_2$-alkyl), $C_1$-$C_{24}$ monoalkylaminosulfonyl-SO$_2$—N(H) alkyl), $C_1$-$C_{24}$ dialkylaminosulfonyl-SO$_2$—N(alkyl)$_2$, $C_5$-$C_{24}$ arylsulfonyl (—SO$_2$-aryl), boryl (—BH$_2$), borono (—B(OH)$_2$), boronato (—B(OR)$_2$ where R is alkyl or other hydrocarbyl), phosphono (—P(O)(OH)$_2$), phosphonato (—P(O)(O)$_2$), phosphinato (P(O)(O—)), phospho (—PO$_2$), and phosphine (—PH$_2$); and the hydrocarbyl moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably C2-C6 alkynyl), $C_5$-$C_{24}$ aryl (preferably $C_5$-$C_{24}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl). Within these substituent structures, the "alkyl," "alkylene," "alkenyl," "alkenylene," "alkynyl," "alkynylene," "alkoxy," "aromatic," "aryl," "aryloxy," "alkaryl," and "aralkyl" moieties may be optionally fluorinated or perfluorinated. Additionally, reference to alcohols, aldehydes, amines, carboxylic acids, ketones, or other similarly reactive functional groups also includes their protected analogs. For example, reference to hydroxy or alcohol also includes those substituents wherein the hydroxy is protected by acetyl (Ac), benzoyl (Bz), benzyl (Bn, Bnl), β-Methoxyethoxymethyl ether (MEM), dimethoxytrityl, [bis-(4-methoxyphenyl)phenylmethyl](DMT), methoxymethyl ether (MOM), methoxytrityl [(4-methoxyphenyl)diphenylmethyl, MMT), p-methoxybenzyl ether (PMB), methylthiomethyl ether, pivaloyl (Piv), tetrahydropyranyl (THP), tetrahydrofuran (THF), trityl (triphenylmethyl, Tr), silyl ether (most popular ones include trimethylsilyl (TMS), tert-butyldimethylsilyl (TBDMS), tri-iso-propylsilyloxymethyl (TOM), and triisopropylsilyl (TIPS) ethers), ethoxyethyl ethers (EE). Reference to amines also includes those substituents wherein the amine is protected by a BOC glycine, carbobenzyloxy (Cbz), p-methoxybenzyl carbonyl (Moz or MeOZ), tert-butyloxycarbonyl (BOC), 9-fluorenylmethyloxycarbonyl (FMOC), acetyl (Ac), benzoyl (Bz), benzyl (Bn), carbamate, p-methoxybenzyl (PMB), 3,4-dimethoxybenzyl (DMPM), p-methoxyphenyl (PMP), tosyl (Ts) group, or sulfonamide (Nosyl & Nps) group. Reference to substituent containing a carbonyl group also includes those substituents wherein the carbonyl is protected by an acetal or ketal, acylal, or diathane group. Reference to substituent containing a carboxylic acid or carboxylate group also includes those substituents wherein the carboxylic acid or carboxylate group is protected by its methyl ester, benzyl ester, tert-butyl ester, an ester of 2,6-disubstituted phenol (e.g. 2,6-dimethylphenol, 2,6-diisopropylphenol, 2,6-di-tert-butylphenol), a silyl ester, an orthoester, or an oxazoline.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one lower substituent group.

In other embodiments of the compounds herein, each substituted or unsubstituted alkyl may be a substituted or unsubstituted $C_{-1}$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and/or each substituted or unsubstituted heterocycloalkyl is a substituted or unsubstituted 3 to 8 membered heterocycloalkyl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, and/or each substituted or unsubstituted heterocycloalkylene is a substituted or unsubstituted 3 to 8 membered heterocycloalkylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, and/or each substituted or unsubstituted heterocycloalkyl is a substituted or unsubstituted 3 to 7 membered heterocycloalkyl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, and/or each substituted or unsubstituted heterocycloalkylene is a substituted or unsubstituted 3 to 7 membered heterocycloalkylene.

By "functionalized" as in "functionalized hydrocarbyl," "functionalized alkyl," "functionalized olefin," "functionalized cyclic olefin," and the like, is meant that in the hydrocarbyl, alkyl, aryl, heteroaryl, olefin, cyclic olefin, or other moiety, at least one hydrogen atom bound to a carbon (or other) atom is replaced with one or more functional groups such as those described herein and above. The term "functional group" is meant to include any functional species that is suitable for the uses described herein. In particular, as used herein, a functional group would necessarily possess the ability to react with or bond to corresponding functional groups on a substrate surface.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

In the context of the instant disclosure, the term "nanoscale" is defined in terms of having at least one dimension less than 1000 nm, preferably less than 100 nm.

"Optional" or "optionally" means that the subsequently described circumstance may or may not occur, so that the description includes separate embodiments where the circumstance occurs and embodiments where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present. Similarly, the phrase "optionally isolated" means that the target material may or may not be separated from other materials used or generated in the method, and, thus, the description includes separate embodiments where the target material is separated and where the target material is not separated, such that subsequence steps are conducted on isolated or in situ generated product.

The terms "method(s)" and "process(es)" are considered interchangeable within this disclosure.

The following listing of embodiments is intended to complement, rather than displace or supersede, any of the previous descriptions.

Embodiment 1. A method comprising irradiating an aggregate of chemically bonded or otherwise associated nanoparticles with a light source capable of providing multiphoton excitation, the light source directed to a focal point volume including (i.e., within or encompassing) the aggregate and having sufficient energy to disrupt or fuse the nanoparticles in the aggregate within the focal point volume to form nanoscale deposits of the nanoparticles. While chemical bonding is one means of forming such aggregates, in certain Aspects of this Embodiment, the aggregate of nanoparticles need not be covalently bonded, but may rather be held in proximity (e.g., according to the metal-metal spacings described elsewhere herein) by confinement by external structures, as described elsewhere herein.

Embodiment 2. The method of Embodiment 1, wherein the nanoparticles comprise metals or metalloids. In certain Aspects of this embodiment, the nanoparticles comprise electrically conducting (pure metals or doped carbon) and semiconducting (including optionally doped Si, GaAs, InP, ZnS, CdS, and PbS) materials.

Embodiment 3. The method of Embodiment 1 or 2, wherein aggregate of nanoparticles comprise titanium, zirconium, gold, silver, palladium, platinum, cerium, arsenic, iron, aluminum, carbon, boron, cadmium, selenium, zinc or silicon, or an alloy or mixture thereof.

Embodiment 4. The method of any one of Embodiments 1 to 3, wherein the nanoparticles titanium, zirconium, gold, silver, platinum, palladium, cerium, arsenic, iron, aluminum, or zinc, or an alloy or mixture thereof. In certain Aspects of this Embodiment, the nanoparticles comprise noble metal plasmonic elements, for example gold, silver, platinum, palladium, or mixtures or alloys thereof.

Embodiment 5. The method of any one of Embodiments 1 to 4, wherein the aggregate of nanoparticles are covalently linked nanoparticles.

Embodiment 6. The method of Embodiment 5, wherein the nanoparticles are bonded together by chemical spacers comprising optionally substituted 2 to 20 membered alkylene or heteroalkylene linkages. In certain Aspects of this embodiment, the nanoparticles are spaced from their next nearest neighbors, on average, in a range of about 1 to 10 nm, typically about 2 nanometers.

Embodiment 7. The method of Embodiment 6, wherein the spacer linkages comprise one or more of —C(O)—, —C(O)O—, —O—, —S—, —NH—, —NR$^1$—, —C(O)NR$^2$—, —S(O)$_n$—, —S(O)NR$^3$—, —OP(O)(OR$^4$)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene, an amino acid sequence linker, or a nucleic acid sequence moiety, where R$^1$, R$^2$, R$^3$, R$^4$, are independently at each occurrence hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n is 1 or 2. In certain Aspects of this Embodiment, the nanoparticles are spaced using strategies, methods, and materials described in U.S. patent application Ser. No. 14/313,736, filed Jun. 24, 2014, in Tam et al. *ACSNano*, 4(4), 2178-2184 (2010)), in Rafal Klajn et al., *Science*, Vol 316 13 Apr. 2007), in Ajlan Al Zaki, et al *ACSNano,* 8(1), 104-112 2014), and in Andrew K. Boal, et al, *Nature* 404 (13), 746-748. April 2000, each of which is incorporated by reference herein for its teaching of strategies and materials.

Embodiment 8. The method of any one of Embodiments 1 to 7, wherein the metallic nanoparticles in the aggregate have a mean particle diameter in a range of from about 2 to 20 nm. Other Aspects of this Embodiment include those ranges described elsewhere herein with respect to this feature.

Embodiment 9. The method of any one of Embodiments 1 to 8, wherein the aggregate of chemically bonded nanoparticles have a mean diameter in a range of from about 15 nm to about 1000 nm. Other Aspects of this Embodiment include those ranges described elsewhere herein with respect to this feature.

Embodiment 10. The method of any one of Embodiments 1 to 9, wherein the aggregate of chemically bonded nanoparticles are dispersed in an aqueous or non-aqueous medium. Other Aspects of this Embodiment include those ranges described elsewhere herein with respect to this feature.

Embodiment 11. The method of any one of Embodiments 1 to 10, wherein the aggregate of chemically bonded nanoparticles is dispersed on a substrate. Other Aspects of this Embodiment include those compositions described elsewhere herein with respect to this feature.

Embodiment 12. The method of any one of Embodiments 1 to 11, wherein the light source is a UV light or a pulsed infrared light. In certain Aspects of this Embodiment, the pulsed infrared light provides femptosecond pulses, as described elsewhere herein.

Embodiment 13. The method of any one of Embodiments 1 to 3, wherein the light source is operating at a power in a range of 10 to 100 mW. Other Aspects of this Embodiment include those ranges described elsewhere herein with respect to this feature.

Embodiment 14. The method of any one of Embodiments 1 to 13, wherein the light source is emitting light at a wavelength in a range of 200 nm to 1500 nm. Other Aspects of this Embodiment include those ranges described elsewhere herein with respect to this feature.

Embodiment 15. The method of any one of Embodiments 1 to 14, wherein irradiating the aggregate comprises scanning the light source across or through the aggregate at a speed in a range of from about 20 to 200 micron/second Embodiment 16. The method of any one of Embodiments 1 to 15, wherein at least one dimension of the nanoscale deposits of the nanoparticles is in a range of from 2 nm to 500 nm. Other Aspects of this Embodiment include those ranges described elsewhere herein with respect to this feature.

Embodiment 17. The method of any one of Embodiments 1 to 16, wherein the resulting nanoscale deposits exhibit optical filtering due to surface plasmon resonances.

Embodiment 18. An optical filter prepared according to the process of any one of claims 1 to 17.

EXAMPLES

The following Examples are provided to illustrate some of the concepts described within this disclosure. While each Example is considered to provide specific individual embodiments of composition, methods of preparation and use, none of the Examples should be considered to limit the more general embodiments described herein.

In the following example, efforts have been made to ensure accuracy with respect to numbers used (e.g. amounts, temperature, etc.) but some experimental error and deviation should be accounted for. Unless indicated otherwise, temperature is in degrees Celsius, pressure is at or near atmospheric.

Example 1

In one example, gold nanoclusters were used, these nanoclusters being prepared and characterized by methods as described in U.S. patent application Ser. No. 14/313,736, filed Jun. 24, 2014, the contents of which are incorporated by reference herein for all purposes, but at least for its teaching of the methods of making chemically linked nanoparticles and the chemically linked nanoparticles themselves. Specifically, the nanocluster aggregates comprised 10 nm diameter Au nanoparticles having an inter-particle spacing of approximately 1-2 nm. The effective nanocluster diameter was approximate diameter 78.5 nm, linked together by a tetrafunctional thiol crosslinker. A drop (approx. volume of 50 microliters) of the solution was put on a cover slip (Thermo Scientific #1.5, 30 mm diameter) and mounted in the oil-immersion mode of the Nanoscribe. The impinging femtosecond laser (790 nm) was turned up to 36 mW and a pre-defined structure was written onto the aggregate-resist. The resultant structures (FIG. 1) were stable to an aqueous wash, suggesting sintering near the glass interface.

Example 2

Figure 2:
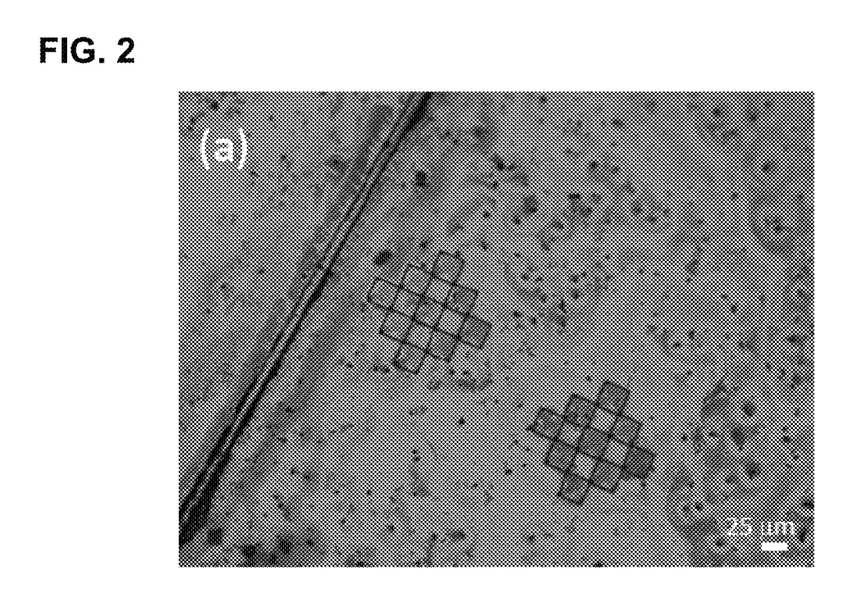

In a second set of experiments, arrays of gold nanorods (length of 5 μm, width of 1 μm and periodicity of 5 μm) were scribed using this technique on a quartz ($SiO_2$) substrate. Some representative optical images are shown below in and FIG. 2(A-C). The features in FIG. 2(C) were 500 nm diameter gold discs with a periodicity of 1 micron on the quartz substrate.

Example 2

Figure 3:
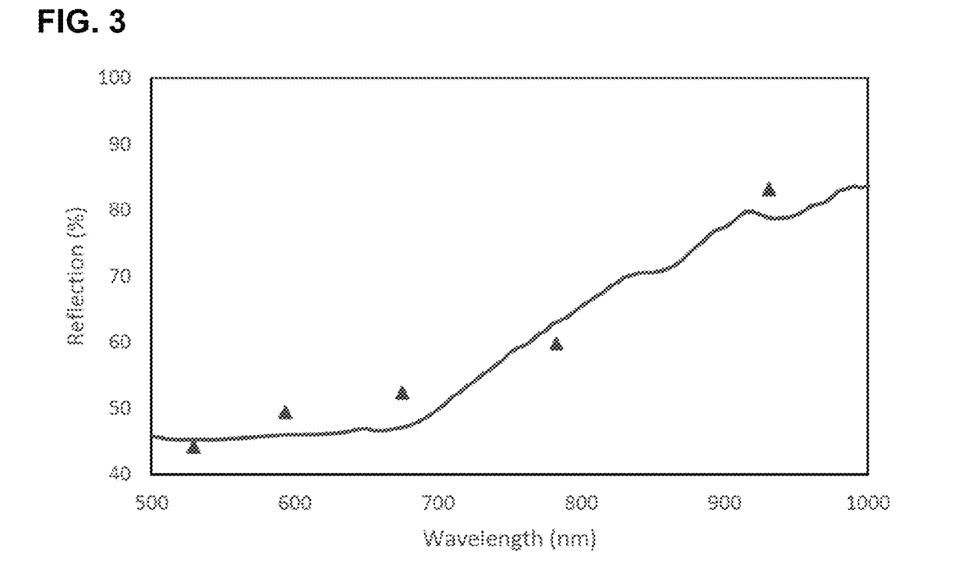
FIG. 3 shows comparison of the experimentally obtained reflection (curve) and full-wave finite-difference time-domain (FDTD) simulation of the results (triangles).

Optical reflection measurements were carried out on these samples of gold nanodiscs and the obtained results have been compared with full-wave numerical FDTD simulations, showing a good fit, as is shown in FIG. 3. The ease of fabrication of these structures over such a large, coupled with the good match between the simulated and experimental demonstrates the great use of this technique for large-scale nanopatterning.

As those skilled in the art will appreciate, numerous modifications and variations of the present invention are possible in light of these teachings, and all such are contemplated hereby. For example, in addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

All of the references cited in this disclosure are incorporated by reference herein in their entireties for all purposes.

What is claimed:

1. A method comprising irradiating an aggregate of chemically bonded or otherwise associated nanoparticles with a light source capable of providing multiphoton excitation, the light source directed at a focal point volume including the aggregate and having sufficient energy to disrupt or fuse the nanoparticles in the aggregate within the focal point volume to form nanoscale deposits of the nanoparticles.

2. The method of claim 1, wherein the nanoparticles comprise metals or metalloids.

3. The method of claim 2, wherein the nanoparticles comprise optionally doped Si, GaAs, InP, ZnS, CdS, or PbS semiconductor materials.

4. The method of claim 1, wherein the nanoparticles comprise titanium, zirconium, gold, silver, palladium, platinum, cerium, arsenic, iron, aluminum, carbon, boron, cadmium, selenium, zinc or silicon, or an alloy or mixture thereof.

5. The method of claim 1, wherein the nanoparticles comprise titanium, zirconium, gold, silver, platinum, palladium, cerium, arsenic, iron, aluminum, or zinc, or an alloy or mixture thereof.

6. The method of claim 5, wherein the nanoparticles comprise gold, silver, platinum, palladium, or a mixture or alloy thereof.

7. The method of claim 1, wherein the aggregate of chemically bonded or otherwise associated nanoparticles comprises chemically bonded nanoparticles that are covalently linked.

8. The method of claim 7, wherein the nanoparticles are bonded together by chemical spacers comprising optionally substituted 2 to 20 membered alkylene or heteroalkylene linkages.

9. The method of claim 8, wherein the spacer linkages comprise one or more of —C(O)—, —C(O)O—, —O—, —S—, —NH—, —NR$^1$—, —C(O)NR$^2$—, —S(O)$_n$—,—S(O)NR$^3$—, —OP(O)(OR$^4$)O—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, an amino acid sequence linker, or a nucleic acid sequence moiety, where R$^1$, R$^2$, R$^3$, and R$^4$ are independently at each occurrence hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n is 1 or 2.

10. The method of claim 1, wherein the nanoparticles have a mean particle diameter in a range of from about 2 to 20 nm.

11. The method of claim 1, wherein the aggregate of chemically bonded or otherwise associated nanoparticles has a mean diameter in a range of from about 15 nm to about 1000 nm.

12. The method of claim 1, wherein the aggregate of chemically bonded or otherwise associated nanoparticles is dispersed in an aqueous solution.

13. The method of claim 1, wherein the aggregate of chemically bonded or otherwise associated nanoparticles is dispersed on a substrate.

14. The method of claim 1, wherein the light source is a UV light or a pulsed infrared light.

15. The method of claim 14, wherein the pulsed infrared light provides femtosecond pulses.

16. The method of claim 1, wherein the light source is operating at a power in a range of 10 to 100 mW.

17. The method of claim 1, wherein the light source is emitting light at a wavelength in a range of 200 nm to 1500 nm.

18. The method of claim 1, wherein irradiating the aggregate comprises scanning the light source through the aggregate or across the aggregate at a speed of 20 to 200 microns / second.

19. The method of claim 1, wherein at least one dimension of the nanoscale deposits of the nanoparticles is in a range of from 2 nm to 500 nm.

20. The method of claim 1, wherein the nanoscale deposits formed exhibit optical filtering due to surface plasmon resonances.

21. An optical filter prepared by the method of claim 1.

22. The method of claim 1, wherein the aggregate comprises nanoparticles that are contained within a micelle, emulsion, microemulsion, or liposome structure.

23. The method of claim 1, wherein the aggregate is dispersed in a non-polar solvent comprising a $C_{1-6}$ alcohol, chloroform, dichloromethane, dimethylformamide, dimethylacetamide, tetrahydrofuran, or 2-methyltetrahydrofuran.

* * * * *